United States Patent [19]

Clarke

[11] 4,379,936

[45] Apr. 12, 1983

[54] NORTROPANE DERIVATIVES

[75] Inventor: Robert L. G. Clarke, Bethlehem, N.Y.

[73] Assignee: Sterling Drug Inc., New York, N.Y.

[21] Appl. No.: 369,545

[22] Filed: Apr. 19, 1982

Related U.S. Application Data

[62] Division of Ser. No. 240,179, Mar. 3, 1981, Pat. No. 4,341,895.

[51] Int. Cl.³ .......................................... C07D 451/02
[52] U.S. Cl. .................................... 546/91; 546/132
[58] Field of Search ................................. 546/91, 132

[56] References Cited

U.S. PATENT DOCUMENTS 3,120,537  2/1964  Archer et al. ..................... 546/132

OTHER PUBLICATIONS

Daum et al., J. Org. Chem. 37, pp. 1665–1669 (1972).
Riley et al., J. Med. Chem. 22, 1167–1171 (1979).
Daum et al., J. Med. Chem. 15, 509–514 (1972).

*Primary Examiner*—R. W. Ramsuer
*Attorney, Agent, or Firm*—Thomas L. Johnson; B. Woodrow Wyatt

[57] ABSTRACT

3α-Benzoylamino-2β-hydroxy-nortropanes substituted in the 8-position by an alkoxycarbonyl or alkanoyl group, useful as analgesics, are prepared by reacting the corresponding 2β,3β-epoxy-nortropane with benzylamine in the presence of phenol.

3 Claims, No Drawings

NORTROPANE DERIVATIVES

This is a division of application Ser. No. 240,179 filed Mar. 3, 1981, now U.S. Pat. No. 4,341,895 issued July 27, 1982.

BACKGROUND OF THE INVENTION (a) Field of the Invention

The invention relates to novel substituted tropane compounds, useful as analgesic agents, and to their preparation.

(b) Description of the Prior Art

Certain tropane derivatives known to the art have been reported to have analgesic activity; namely, 3-phenyl-3-carboxytropane (Archer et al. U.S. Pat. No. 3,120,537, Feb. 4, 1964); and 3-(N-propionylanilino)-8-(2-phenylethyl)-nortropane [Riley et al., J. Med. Chem. 22, 1167–71 (1979)].

SUMMARY OF THE INVENTION

In its product aspect, the invention relates to compounds of the formula:

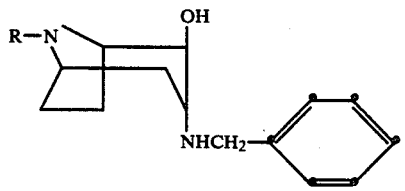

where R is alkoxycarbonyl or alkanoyl having from two to four carbon atoms; or pharmaceutically acceptable acid-addition salts thereof.

In its process aspect, the invention relates to a process for preparing a compound of formula I which comprises reacting a compound of the formula:

with benzylamine in the presence of phenol.

In a further product aspect, the invention relates to the novel intermediates of formulas II and III where R is alkanoyl having from two to four carbon atoms.

DETAILED DESCRIPTION INCLUSIVE OF PREFERRED EMBODIMENTS

The preparation of a compound of formula I by reacting a compound of formula II with benzylamine in the presence of phenol is carried out by heating the reactants at a temperature between about 150° C. and 250° C.

The intermediates of formula II are in turn prepared by epoxidation of nortropidine compounds of the formula:

The compounds of formula III where R is alkoxycarbonyl are a known class of compounds [Daum et al., J. Org. Chem. 37, 1665–9 (1972)], and the compounds of formula III where R is alkanoyl are prepared by reacting nortropidine with a lower-alkanoyl chloride.

The invention contemplates the compounds of formula I in both the free base form and acid-addition salt form. The acid-addition salts are formed by reacting the free base with an equivalent amount of an acid the anion of which is non-toxic to animal organisms. Examples of appropriate acid-addition salts are the hydrochloride, hydrobromide, sulfate, bisulfate, p-toluenesulfonate, methanesulfonate, naphthalenesulfonate and cyclohexanesulfamate salts.

The compounds of formula I and their acid-addition salts are useful as analgesic agents, as determined by standard tests performed on the compounds of formula I where R is ethoxycarbonyl and propionyl in the form of their p-toluenesulfonate salts. The test data are set forth in the following table:

TABLE[a]

| Compound | Tail Flick ED$_{50}^{bc}$ | Antagonist[d] | ACh ED$_{50}$[e] |
|---|---|---|---|
| I (R = C$_2$H$_5$COO) | 56 ± 4 | inactive (10 & 80) | 6.9 (2.2–31) |
| I (R = C$_2$H$_5$CO) | 44 ± 3.5 | inactive (10) | 16 (12–20) |

| Compound | Bradykinin ED$_{50}$[f] | Straub Tail[g] |
|---|---|---|
| I (R = C$_2$H$_5$COO) | 21 (11–40)[h] | 75[i] |
| I (R = C$_2$H$_5$CO) | Not Done | 30 & 60[i] |

[a]All activities are expressed in mg/kg s.c., free base.
[b]Determined in rat by method of L.S. Harris and . K. Pierson, J. Pharmacol. Exp. Ther. 143, 141 (1964).
[c]Prevented by nalorphine at 1.0 mg.kg s.c.
[d]The activity vs. phenazocine tested in rat by procedure of Harris and Pierson, reference in footnote b.
[e]Procedure (in mouse) of H.O.J. Collier, L.C. Dineen, C.A. Johnson and C. Schneider, Br. J. Pharmacol. Chemother. 32, 295 (1968).
[f]G. Defenu, L. Pegrassi and B. Lumachi, J. Pharm. Pharmacol. 18, 135 (1966); B.A. Berkowitz and E.L. Way, J. Pharmacol. Exp. Ther. 177, 500 (1971); measured in rat.
[g]Observed in mouse.
[h]Mild depression at 10; depression at 20 and 30.
[i]Increased locomotor activity.

The compounds can be prepared for use by dissolving the free base form in an oil medium or an acid-addition salt form in an aqueous medium for parenteral administration; or by incorporating the free base form or acid-addition salt form with conventional solid excipients to afford a solid formulation suitable for oral administration.

The following examples will further illustrate the invention.

EXAMPLE 1

(a) Ethyl 2β,3β-epoxynortropane-8-carboxylate [ethyl (exo)-2,3-epoxy-8-azabicyclo[3.2.1]octane-8-carboxylate] (II; R=C$_2$H$_5$COO)

A stirred mixture of 43.5 g (0.32 mol) of sodium acetate trihydrate, 2.1 L of acetic acid and 475 g of 40% peracetic acid was treated at room temperature with 150 g (0.83 mol) of ethyl nortropidine-8-carboxylate (III; R=C$_2$H$_5$COO) in a rapid stream of drops. No heat was evolved. After standing overnight the mixture was concentrated at <35° C. in vacuo and the residual paste was treated with excess 35% sodium hydroxide solution. The product was extracted with 6 portions of ether and distilled, the portion boiling at 106°–109° C. (0.6 mm) (125 g) being the desired epoxide. It was stirred with 300 mL of pentane and the material which crystallized collected to give 119.0 g (73%) of II (R=C$_2$H$_5$COO), m.p. 52°–54° C. This compound, prepared by a different process, is described by S. J. Daum et al., J. Med. Chem. 15, 509–14 (1972).

(b) Ethyl 3α-benzylamino-2β-hydroxy-1αH,5αH-nortropane-8-carboxylate [ethyl (2-exo-3-endo)-2-hydroxy-3-[(phenylmethyl)amino]-8-azabicyclo[3.2.1]octane-8-carboxylate] (I; R=C₂H₅COO)

A mixture of 22.0 g (0.11 mol) of ethyl 2β,3β-epoxynortropane-8-carboxylate, 23.1 g (0.22 mol) of benzylamine and 5.2 g (0.055 mol) of phenol was heated at 180°–190° C. for 4 hours, cooled, and diluted with 150 mL of 2 N hydrochloric acid and ether. The ether was washed with 2 N hydrochloric acid and discarded. The combined acid layers were made basic with 35% sodium hydroxide and the liberated base was separated with ether. This 42.0 g of product was chromatographed on 1.2 kg of silica gel using 7 L of 1:49:50 i-propylamine-ether-pentane for development followed by 3 L of 1:64:35 mixture and, finally, 8 L of 1:99 i-propylamine-ether. The last 7 L of eluate was treated with gaseous carbon dioxide and the precipitated benzylamine carbonate was removed by filtration. Concentration of the filtrate gave 13.8 g (41%) of oily compound I (R=C₂H₅COO).

The p-toluenesulfonate salt of I (R=C₂H₅COO) formed prisms from acetonitrile which softened about 145° C. and then melted at 173°–175° C. with intumescence.

By replacing the ethyl nortropidine-8-carboxylate in part (a) above by a molar equivalent amount of methyl nortropidine-8-carboxylate, propyl nortropidine-8-carboxylate, or isopropyl nortropidine-8-carboxylate, it is contemplated that there can be prepared, respectively, methyl 3α-benzylamino-2β-hydroxy-1αH,5=H-nortropane-8-carboxylate (I; R=CH₃COO); propyl 3α-benzylamino-2β-hydroxy-1αH,5αH-nortropane-8-carboxylate (I; R=CH₃CH₂CH₂COO) or isopropyl 3α-benzylamino-2β-hydroxy-1αH,5=H-nortropane-8-carboxylate (I; R=(CH₃)₂CHCOO).

EXAMPLE 2

(a) N-Propionylnortropidine [8-(1-oxopropyl)-8-azabicyclo[3.2.1]-oct-2-ene] (III; R=C₂H₅CO)

A solution of 68.5 g (0.628 mol) of nortropidine in 100 mL of water at 5° C. was treated simultaneously with 630 mL (1.26 mol) of 2 N sodium hydroxide and 630 mL of a solution containing 117 g (1.26 mol) of propanoyl chloride in methylene dichloride with vigorous stirring at 5° to 10° C. during 2.5 hours. The layers were separated and the water layer was saturated with salt and extracted twice with methylene dichloride. The combined organic layers were concentrated and the residual oil was distilled. The resulting III (R=C₂H₅CO) was collected at 83°–108° C. (0.6 to 2.5 mm), 103 g, 100%. Tlc and vpc on the product showed only a single spot and peak respectively.

(b) 2β,3β-Epoxy-N-propionylnortropane [(exo)-2,3-epoxy-8-(1-oxopropyl)-8-azabicyclo[3.2.1]octane] (II; R=C₂H₅CO)

To a solution of 33.8 g (0.249 mol) of sodium acetate trihydrate in 1.5 L of water was added 368 g of 40% peracetic acid. The solution was cooled to 10° C. and treated with 115.6 g (0.70 mol) of III (R=C₂H₅CO) during 10 min with stirring, then left overnight at 5° C. Solid sodium sulfite (250 g) was added portionwise, causing the mixture finally to give a negative starch-iodide test. The mixture was filtered and the filtrate was concentrated at room temperature at an oil pump. Dilution of the residual paste with ether, filtration, washing of the filtrate with 35% sodium hydroxide and concentration gave an oily product which was distilled. The portion which boiled at 82°–113° C. (0.3 mm) was collected and redistilled to give 50.5 g (40%) of II (R=C₂H₅CO), b.p. 105°–108° C. (0.3 mm), impurity by tlc <3%. This product was used without further treatment.

(c) 3α-Benzylamino-8-propionyl-1αH,5αH-nortropan-2β-ol [(2-exo-3-endo)-8-(1-oxopropyl)-3-(phenylmethylamino)-8-azabicyclo[3.2.1]-octan-2-ol] (I; R=C₂H₅CO)

A mixture of 25.0 g (0.138 mol) of II (R=C₂H₅CO) from part (b) above, 29.0 g (0.27 mol) of benzylamine and 6.6 g (0.07 mol) of phenol was heated at 175° C. for 4 hours. The phenol and the excess benzylamine were removed by an oil pump using a bath temperature of 150° C. The residual oil in ether was washed with 75 and 25 mL of 2 N hydrochloric acid and the washings were made basic with 35% sodium hydroxide. The liberated base, which was separated with ether, crystallized to a waxy solid. Trituration of the solid with 4 portions of pentane and 2 portions of 15:85 ether-pentane afforded 24.0 g (60%) of I (R=C₂H₅CO).

The p-toluenesulfonate salt of I (R=C₂H₅CO) was prepared in ethyl acetate solution and melted at 191°–194° C. when recrystallized from ethanol.

By replacing the propanoyl chloride in part (a) of Example 2 by a molar equivalent amount of acetyl chloride, butyryl chloride or isobutyryl chloride, it is contemplated that there can be prepared, respectively, 3α-benzylamino-8-acetyl-1αH,5αH-nortropan-3β-ol (I; R=CH₃CO); 3α-benzylamino-8-butyryl-1αH,5αH-nortropan-3β-ol (I; R=CH₃CH₂CH₂CO); or 3α-benzylamino-8-isobutyryl-1αH,5αH-nortropan-3β-ol (I; R=(CH₃)₂CHCO).

I claim:
1. A compound of the formula

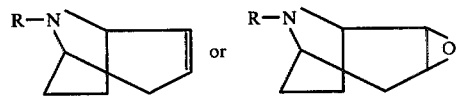

wherein R is alkanoyl having from two to four carbon atoms.
2. 2β,3β-Epoxy-N-propionylnortropane, according to claim 1.
3. N-Propionylnortropidine, according to claim 1.

* * * * *

UNITED STATES PATENT AND TRADEMARK OFFICE
CERTIFICATE OF CORRECTION

PATENT NO. : 4,379,936
DATED : April 12, 1983
INVENTOR(S) : Robert La Grone Clarke It is certified that error appears in the above-identified patent and that said Letters Patent are hereby corrected as shown below:

Column 2, line 28, ".K. Pierson" should read --A.K. Pierson--.

Column 2, line 33, "G. Defenu" should read --G. Deffenu--.

Column 3, lines 39 and 44, "1αH,5=H" should read --1αH,5αH--, each occurrence.

Signed and Sealed this

Ninth Day of August 1983

[SEAL]

Attest:

GERALD J. MOSSINGHOFF

Attesting Officer     Commissioner of Patents and Trademarks